United States Patent [19]

Chastang et al.

[11] Patent Number: 4,585,348
[45] Date of Patent: Apr. 29, 1986

[54] ULTRA-FAST PHOTOMETRIC INSTRUMENT

[75] Inventors: Jean-Claude A. Chastang, Mahopac; Walter W. Hildenbrand, Brewster; Menachem Levanoni, Yorktown Heights, all of N.Y.

[73] Assignee: International Business Machines Corporation, Armonk, N.Y.

[21] Appl. No.: 573,783

[22] Filed: Jan. 25, 1984

Related U.S. Application Data

[63] Continuation-in-part of Ser. No. 306,559, Sep. 28, 1981, abandoned.

[51] Int. Cl.$^4$ .............................................. G01N 21/21
[52] U.S. Cl. ....................................................... 356/369
[58] Field of Search ........................................ 356/369

[56] References Cited

U.S. PATENT DOCUMENTS

| | | | |
|---|---|---|---|
| 3,060,793 | 10/1962 | Wells | 356/369 |
| 3,653,767 | 4/1972 | Liskowitz | 356/102 |
| 3,904,293 | 9/1975 | Gee | 356/118 |
| 3,995,957 | 12/1976 | Pilloff | 356/114 |

OTHER PUBLICATIONS

Chwalow et al., "Automatic Brewster's Angle Thin Film Thickness Measurement Spectrophotometer", IBM Tech. Disc. Bull., 1-1978, pp. 3133-3134.

Smith, N., "Optical Constants of Sodium & Potassium From 0.5 to 4.0 eV by Split-Beam Ellipsometry", Phys. Review, 7-1969, pp. 634-644.

Smith, T., "An Automated Scanning Ellipsometer", Surface Science, 6-1976, pp. 212-220.

Hunderi et al., "A Simple Automatic Ellipsometer for A Wide Energy Range", Surface Science, 6-1976, pp. 182-188.

*Primary Examiner*—William H. Punter
*Attorney, Agent, or Firm*—Graham S. Jones, II; Alexander Tognino

[57] ABSTRACT

This is a static photometric polarimeter for use with a sample S upon which a beam passed through a beam splitter (which reflects the beam to a detector $D_o$) and which beam is 45° polarized. The reflection of the beam from the surface of sample S is passed to a polarizing beam splitter with one portion of the reflected beam going to a detector $D_s$ which measures the perpendicular polarization component of the beam and the other portion of the beam going to the detector $D_p$ which measures the parallel polarized portion of the reflected beam.

7 Claims, 13 Drawing Figures

BASIC PHOTOMETRIC ELLIPSOMETER

ULTRA-FAST PHOTOMETRIC INSTRUMENT

This is a continuation-in-part of U.S. Ser. No. 6/306,559, filed Sept. 28, 1981, and now abandoned.

BACKGROUND OF THE INVENTION

1. Field of the Invention

This invention relates to polarimetry and ellipsometry. More particularly, it relates to a novel static polarimeter requiring less hardware while providing improved accuracy, and a smaller beam size.

2. Description of the Prior Art

T. Smith wrote an article entitled "An Automated Scanning Ellipsometer" in Surface Science 56, No. 1, 212–220 (June 1976) which shows an automated ellipsometer in FIG. 1 thereof with a polarized beam splitter 4 which supplies a fraction of the beam from the light source 1. The beam, which passes through the polarizer, is reflected from the surface of a sample. A portion of the reflected beam reaches a 45° analyzer prism 6 and it is measured by a detector 8. Another portion of the reflected beam 7 reaches a second analyzer prism which splits the portion of the reflected beam it receives into parallel p and perpendicularly s polarized segments. There are detectors connected to receive the separate p and s segments. It should be noted that the prism 6 and the prism 7 are separate but juxtaposed. Accordingly, some of the light in the beam reflected from the surface of the sample S may not be received by any one of the three detectors 8, 9, and 10.

In addition, three detectors are used to measure the reflected beam rather than the two detectors required in our system. Furthermore, since the beam is split from side to side, the detectors are dependent upon the uniformity of the beam from side to side. Smith requires careful alignment of the beam.

The sources of error in Smith overcome by the present arrangement are (1) alignment of the beam; (2) uniformity of the beam, and (3) uniformity of the sample. In addition, the present arrangement permits focussing upon sample object surface areas as small as 1 mil$^2$ whereas Smith cannot, since his error is on the order of a few mils$^2$, Smith states that he requires uniform illumination (p. 219) and a large area (p. 213).

At page 220 of the Smith article under comments made at the conference where the article was presented, it is stated by M. J. Dignam "Rather than having two beams, we had in mind placing a reflected beam splitter with plates at normal incidence and then analyzing each of the beams with a polarizing splitter as you have done. The polarizing beam splitter is properly oriented to get all the information from a single beam. You still have the calibration problems and the calibration of the beam splitter but I think it can be done with a single beam". That arrangement would use four detectors at the output end in place of the three detectors of Smith and the two detectors employed here as we interpret that statement made by M. J. Dignam. The result is a more complex set of twice as many data outputs, and five detectors instead of three with the attendant disadvantages of more sources of error and cost of computation. The present system employs a novel technique, which permits use of only three detectors, whereas heretofore, it had been believed that four detectors would be required.

SUMMARY OF THE INVENTION

In accordance with this invention an instrument is provided comprising a source of a polarized light beam directed towards a sample position. Means is provided for supporting a sample in the sample position. A polarizing beam splitter is supported for reception of the reflection of the beam from the surface of a sample in the sample position and a pair of detectors for p and s beams is positioned to receive the p and s portions of said light beam from the polarizing beam splitter. Preferably the source includes means for polarization of the light beam, which preferably polarizes the light beam at 45° to the plane of incidence, or provides circular polarization of the light beam. Preferably a beam splitter splits the light beam and directs a portion thereof to a third detector and directs the remainder of the light beam to the sample.

Further, in accordance with this invention, an instrument comprises a source of a polarized light beam directed towards a beam splitter. A portion of the light beam split thereby passes to a normalizing detector and the remainder thereof passes to a sample position adapted for holding a sample to be measured. Means is provided for supporting a sample in the sample position. A polarizing beam splitter is supported for reception of the reflection of the beam from the surface of a sample in the sample position. A pair of detectors for p and s beams is positioned to receive the p and s portions of the light beam from the polarizing beam splitter.

Preferably the first beam splitter reflects the beam towards the sample and transmits the remainder of the beam to the normalizing detector, or the beam splitter reflects the beam towards the normalizing detector and transmits the remainder of the beam to the sample.

DESCRIPTION OF THE PREFERRED EMBODIMENT

Figure 1:
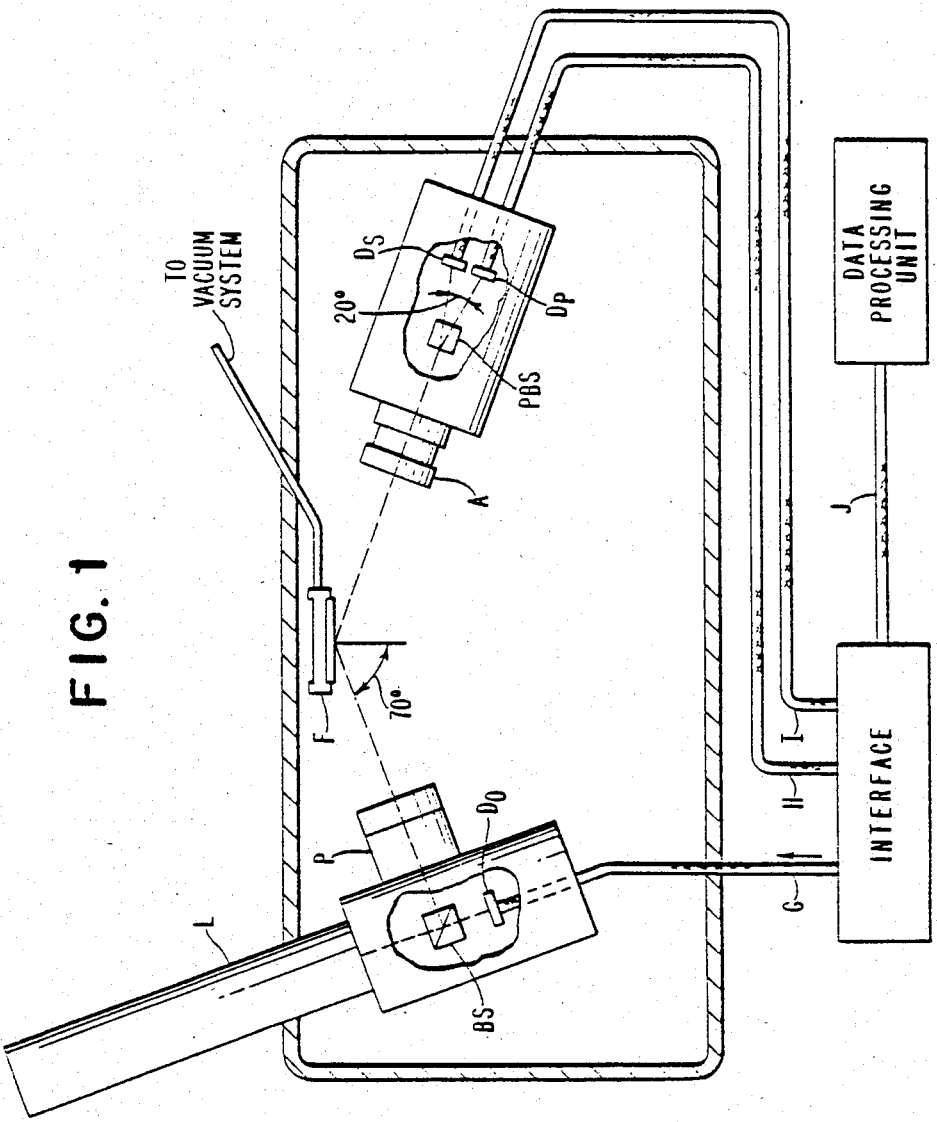
FIG. 1 shows an optical polarimeter system in accordance with this invention.

FIG. 1 shows a chamber containing sample S held in place on fixture F by means of pressure induced by vacuum line A. A laser L (in this particular case shown as about eleven inches long) is directed towards beam splitter BS which passes a portion of the beam to photodiode $D_o$ and reflects the remainder of the beam towards the sample S. The beam reflected from beam splitter BS passes through polarizer P. In principle polarizer P can be omitted since the laser beam is polarized. Polarizer P enhances the polarization. The beam is directed at the sample at an angle $\phi$ of 70° with respect to a line normal to the surface of the sample S. Angles which are preferred range from a few degrees to close to 90°. At 45° a measurement of a single interface cannot be done but a multiple layer structure can be measured. The beam reflected from the surface of the sample is passed through aperture A (which eliminates spurious light) to a polarizing beam splitter PBS (comprising preferably a Wollaston prism) which produces a first beam directed to the photodiode $D_p$ and a second beam directed to a second photodiode $D_s$ with the two beams separated in the plane defined by the beams by an angle of 20°. Any angle can be used, but larger angles are preferred in a practical application. The outputs of sensor $D_o$, sensor $D_p$ and sensor $D_s$ pass through lines G, H and I respectively to the interface which is connected by cable J to the data processing unit. As will be explained below, the polarizing beam splitter produces two different polarizations of the beam for the two photodiodes $D_p$ and $D_s$.

The polarimeter of the instant invention is an instrument of the static photometric type and its resolving time is limited only by the rise times of its photodetectors.

As an alternative, beam splitter BS and sensor $D_o$ can be omitted if a standard reference sample is available to calibrate measurements. The purpose of beam splitter BS and sensor $D_o$ is to eliminate the effects of variation of the intensity of the laser beam from laser L.

Figure 2:
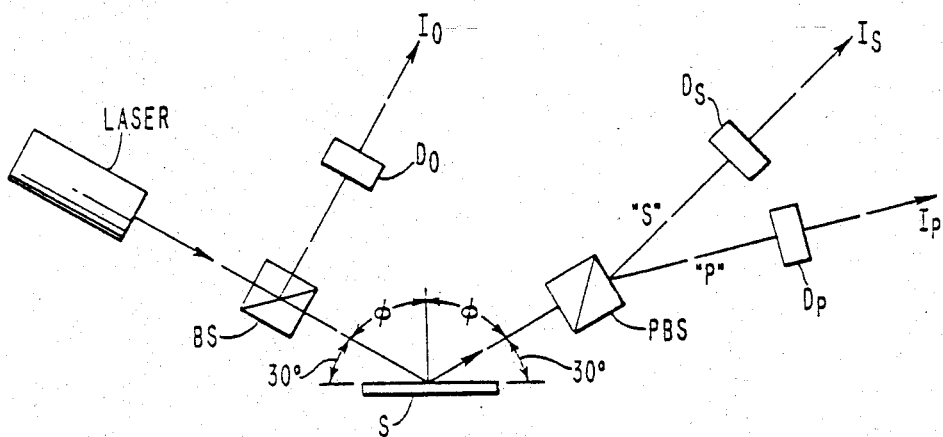
FIG. 2 shows a schematic diagram of an optical arrangement and sensors in a modified polarimeter system in accordance with this invention.

The polarimeter, shown in FIG. 2, utilizes a single polarized beam (polarized, say, at 45° to the plane of incidence) from a small HeNe laser L (or any other collimated beam in combination with a polarizer). A beam splitter BS directs a fraction of the incident beam to normalizing detector $D_o$. A polarizing beam splitter PBS (such as a Wollaston prism) splits the reflected beam from sample S into its "p" (parallel) and "s" (perpendicular) polarization components which are then monitored by detectors $D_p$ and $D_s$.

From the light intensities, $I_o$, $I_p$ and $I_s$, recorded by detectors $D_o$, $D_p$ and $D_s$, the "p" and "s" intensity reflection coefficients $R_p$ and $R_s$ can be derived. For example, for light polarized at 45° and an incident beam splitting ratio of 1:2 (i.e., $I_o$ equals one-third of the source beam intensity), the intensity reflection coefficients are given by $$R_p = \frac{I_p}{I_o} \text{ and } R_s = \frac{I_s}{I_o}$$

It is shown in equations below that knowledge of $R_p$ and $R_s$ is sufficient to determine the polarization state of the reflected light (or equivalently, the complex index of refraction of the sample). This statement is valid for all angles of incidence other than 0° (normal incidence), 45° and 90° (grazing incidence). Since there is no mechanical motion during the operation of this instrument and the needed optical information is recorded by three stationary photodetectors, the response time of the ellipsometer is determined solely by the detectors rise times which can be very small. Therefore, this instrument measures variations in refractive indices and extinction coefficients in very rapid time scales.

The measurement accuracy of this device is highly dependent on its photodetectors. Highly linear detectors (such as solid state photodiodes) are necessary for good performance. In the absence of a computer the detectors should be accurately calibrated and matched. However, variations in source intensity are cancelled out since only intensity ratios are used in data reductions.

Instead of a plane polarized incident beam, a circularly polarized beam can be used. A ¼ wavelength plate suitably oriented will convert any plane polarized light to circular polarization. This will not affect the operation of the ellipsometer because the only difference is 90° of phase delay between the "p" and "s" polarized components which does not affect the photodetectors. The results are identical to those obtained using a 45° polarized incident beam.

In an experimental device, samples were measured with reasonable accuracy at an incident angle of 70°. These included dielectrics (glasses), semiconductors (silicon) and conductors (gold and titanium). The source was a 5 mw HeNe laser and the detectors were (photodiode/Op-amp combinatins) with a rise time of about 100 nanoseconds. The intensity reflection coefficients $R_p$ and $R_s$ could be observed directly through the use of two digital ratiometers. Practical applications of this invention include measurements of values as follows:

1. Optical changes in materials undergoing short intense heat pulses.
2. Optical changes in materials undergoing fast chemical/physical reaction.
3. High resolution film growth rates on substrates.

In general, this inventin provides a fast response, general purpose polarimeter (simple design, no moving parts).

Figure 3:
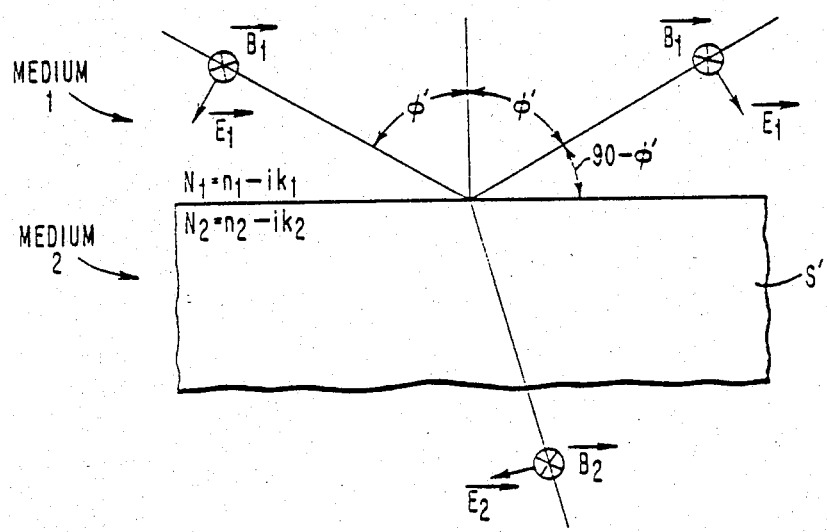
FIG. 3 shows beams of light refracted and reflected at an interface with p polarization.

The amplitude reflection coefficients for plane polarized light are given by Fresnel Eqns. (Ref. 1):

$$r_s = \frac{N_1\cos\phi - \sqrt{N_2^2 - N_1^2\sin^2\phi}}{N_1\cos\phi + \sqrt{N_2^2 - N_1^2\sin^2\phi}} = \frac{\cos\phi - \sqrt{N^2 - \sin^2\phi}}{\cos\phi + \sqrt{N^2 - \sin^2\phi}} \quad (1)$$

$$r_p = \frac{N_2^2\cos\phi - N_1\sqrt{N_2^2 - N_1^2\sin^2\phi}}{N_2^2\cos\phi + N_2\sqrt{N_2^2 - N_1^2\sin^2\phi}} = \frac{N^2\cos\phi - \sqrt{N^2 - \sin^2\phi}}{N^2\cos\phi - \sqrt{N^2 - \sin^2\phi}} \quad (2)$$

where $r_s$ and $r_p$ are the amplitude reflection coefficients, $N_1$ and $N_2$ are the indices of refraction of the media (light is incident from medium 1 onto medium 2) and $\phi$ is the angle of incidence as shown in FIG. 3.

FIG. 3 shows reflection and refraction at an interface with p polarization. $N = N_2/N_1$ is the relative index of refraction. In order to include absorption, $N_1$, $N_2$ and $N$ are complex numbers and have the form $N = n - ik$ where n is the (real) index of refraction and k is known as the extinction coefficient. From equation 1, N can be expressed in terms of $r_s$ as:

$$N^2 = 1 - 4\frac{r_s}{(1+r_s)^2}\cos^2\phi \quad (3)$$

Using equations 2 and 3, $r_p$ can be derived as:

$$r_p = r_s\frac{r_s - \cos 2\phi}{1 - r_s\cos 2\phi} \text{ (or equivalent)} \quad (4)$$

$$r_p = \frac{\tan^2\phi - \frac{1-r_s}{1+r_s}}{\tan^2\phi + \frac{1-r_s}{1+r_s}}$$

Equation 4 can now be used to yield $$\cos\sigma_s = \frac{R_s - \frac{R_p}{R_s} + (1-R_p)\cos^2 2\phi}{2R_s^{\frac{1}{2}}\left(1 - \frac{R_p}{R_s}\right)\cos 2\phi} \quad (5)$$

where $\sigma_s$ is the "s"-polarization phase shift on reflection (i.e., $r_s = |r_s|e^{i\sigma_s}$ and $R_p$, $R_s$ are the "p" and "s" polarization intensity reflection coefficients respectively given by $R_p = |r_p|^2$ and $R_s = |r_s|^2$.

Knowledge of $R_p$, $R_s$ and $\phi$ is therefore sufficient to determine both the amplitude phase of the "s"-polarization amplitude reflection coefficient-$r_s$ and therefore also $N = n - ik$ (using equation 3). The "p"-polarization amplitude reflection coefficient-$r_p$ can also be determined using equation 4.

Note that at an angle of $\phi = 45°$, equation 4 yields $r_p = r_s^2$ and equation 5 cannot be used to determine the "s"-polarization phase shift.

$$\left(\cos\sigma_s \xrightarrow{\phi \to 45°} \frac{0}{0}\right).$$

Figure 4:
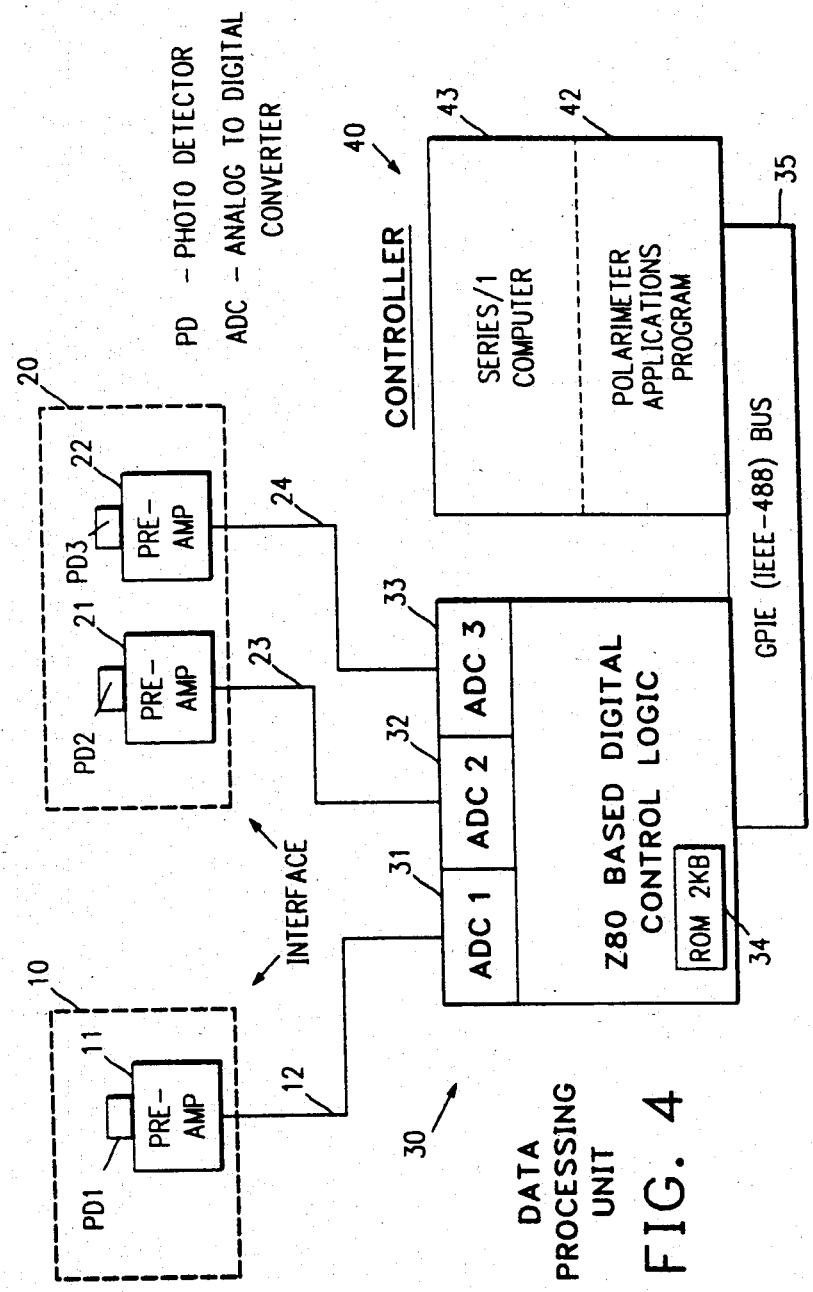
FIG. 4 is a schematic diagram of the system in accordance with this invention.

FIG. 4 shows a schematic diagram of a preferred embodiment of the interface and the data processing unit of FIG. 1 modified in the sense that the interface has been split into two units which are incorporated into hardware inside the chamber shown in FIG. 1.

The portion of the interface which reads the signal $D_O$ is photodetector PD1 which is mounted upon a circuit board with preamplifier 11, which is connected by cable 12 to analog to digital converter ACD1 in the data processsing unit 30. Data processing unit 30 comprises three analog to digital converters ACD1, ACD2, and ACD3 plus a Z80 based digital control logic comprising a single chip microprocessor which is a Zilog unit (which could also be a Mostek Z80 unit), and a 2 kilobit ROM 34 which contains hardware required to operate the control logic, a 4 kilobyte RAM which provides intermediate storage for the converted photodetector signals, and other digital integrated circuits. Each of the analog-to-digital converters is 12 bits wide. The remainder of the interface comprises block 20 including units which read the $D_S$ and $D_P$ are photodetectors PD2 and PD3 respectively, which are connected to preamplifiers 21 and 22 respectively which are connected to lines 23 and 24 to converter units ACD2 and ACD3.

The data processing unit is connected to a host computer or controller 40 by means of a standard IEEE-488 Bus which is known as a General Purpose Interface Bus (GPIB). The controller 40 preferably includes a Series/1 IBM computer 43 which includes polarimeter applications programs 42. In operation, the buffer memory is unloaded to the Series/1 or PC computer 43, with 1536 bytes of data being transmitted. It is split by the applications program with six bytes being required for each information entitity of twelve bits per parameter with six bits left over, since two bytes are required to carry the 12 bits. We have 256 such entries.

If there is noise, the Z80 must repeat the 256 measurements. Noise is noted by a measurement of a wide standard deviation. With a film one has an alpha refraction which varies a function of thickness.

I. Ultrafast Polarimeter (UPF)

Manufacturing facilities for Large Scale Integration (LSI) chips rely heavily on thin film processes which require tight controls of film deposition and film etching. This need is expected to require increased capabilities in film thickness monitoring and control in the future.

Currently, control of film deposition in sputtering chambers and high-temperature furnaces is achieved (indirectly) via time and power or temperature calibration since crystal monitors cannot be used in these cases. This technique is not very accurate, requires an individual calibration curve for each chamber or furnace, and is sensitive to variations in deposition (or etching) conditions.

The Ultrafast Polarimeter (UPS) of this invention is a static photometric polarimeter for online, realtime film thickness monitoring and control. The UFP provides direct tracking of film thickness (deposition or removal) as well as film optical index of refraction. The instrument utilizes a laser probing beam and simple optical detection scheme to monitor the reflected light from the tracked sample. It then converts the reflected intensities to the desired film parameters (thickness and refractive index).

The UFP is a static instrument and does not require mechanical motion for operation (commercial ellipsometers do). Consequently, it is capable of high-speed operation with a resolving time limited only by its photodetector's response. The instrument is completely automated and can be driven by any micro/mini-computer (via the IEEE-488 interface bus) which controls data acquisition, data reduction, and display of results.

The modular UFP design makes it easily adaptable to a variety of online configurations used in Manufacturing. It is mounted externally to the chamber where film deposition (or etching) takes place and does not interfere with tool operation. The instrument has been successfully tested both offline and online on a sputtering chamber ($Al_2O_3$ deposition) and on an oxidation furnace ($SiO_2$ growth, silicon facility).

In Section II, the concepts of ellipsometry and polarimetry are reviewed and the UFP concept is introduced. Section III describes the UFP including its three functional sections; its operation, the software package, and error analysis. Section IV presents experimental results (offline and online) as well as performance evaluation. Section V is devoted to applications (current and future).

For a more complete treatment of the topics of ellipsometry and polarimetry, the reader is referred to the excellent monogram, *"Ellipsometry and Polarized Light,"* by R. M. A. Azzam and N. M. Bashara, North Holland Publishing Co., 1977.

II. ELLIPSOMETRY AND POLARIMETRY

The simplest, and effectively the only, method for direct determination of the optical constants of materials, as well as direct film thickness measurement, is based on the observation of reflected light intensity and its state of polarization. When a linearly polarized light wave is incident on a surface, the reflected light will, in general, be elliptically polarized. This ellipticity is due to a phase difference which takes place on reflection between the two polarization components of the reflected beam. This polarization ellipse, in effect, characterizes the optical properties of the reflecting surface. Consequently, measurement of the orientation and eccentricity (i.e., phase difference) of the polarization ellipse can be used to derive the optical properties of the reflecting surface. Surface films also affect the reflected polarization ellipse, in a more complicated way, involving film thickness as well as its optical constants. Therefore, film parameters such as thickness and index of refraction can also be determined in appropriate cases.

A. Ellipsometry

Instruments which derive the optical properties of surfaces from direct measurement of the parameters of the sample-reflected polarization ellipse are called ellipsometers. Conventional ellipsometers have evolved into two major practical types—null ellipsometers and photometric ellipsometers. Other types have been introduced but have not gained wide acceptance due mainly to special limitations, complexity, and high cost.

Figure 5:
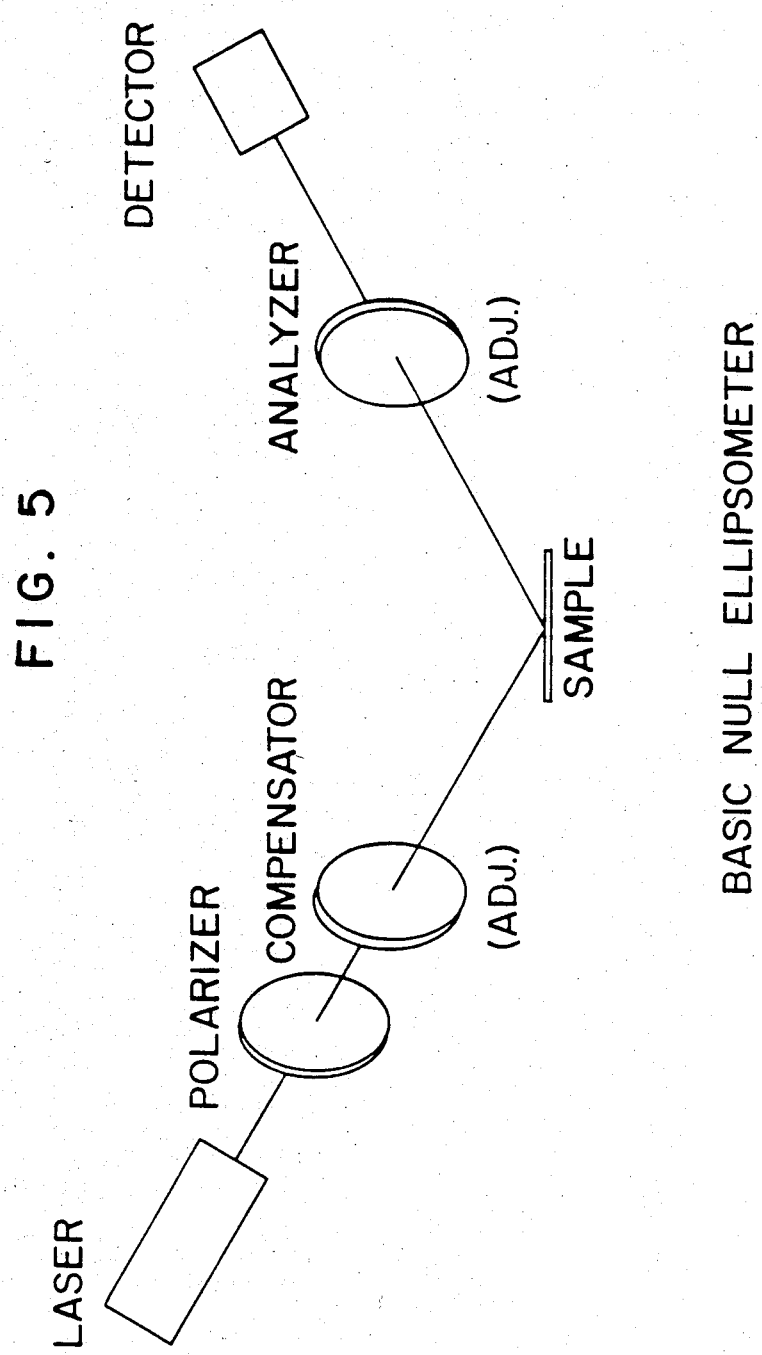
FIG. 5 is a diagram of a system of null ellipsometry.

Null ellipsometry (FIG. 5) is based on direct measurement of a set of azimuth angles for the polarizer, compensator, and analyzer such that the light flux reaching the photodetector is extinguished. Normally, the polarizer is fixed at a convenient angle while the compensator's retardation angle and the analyzer azimuth angle are adjusted (manually or automatically) for a null or minimum condition. From the measured angles, the ellipsometric parameter $\psi$ (ellipse orientation) and $\Delta$ (elliptical phase difference) are simply obtained. The sample's optical properties are then computed using an appropriate material structure model (i.e., single interface, film, etc).

Figure 6:
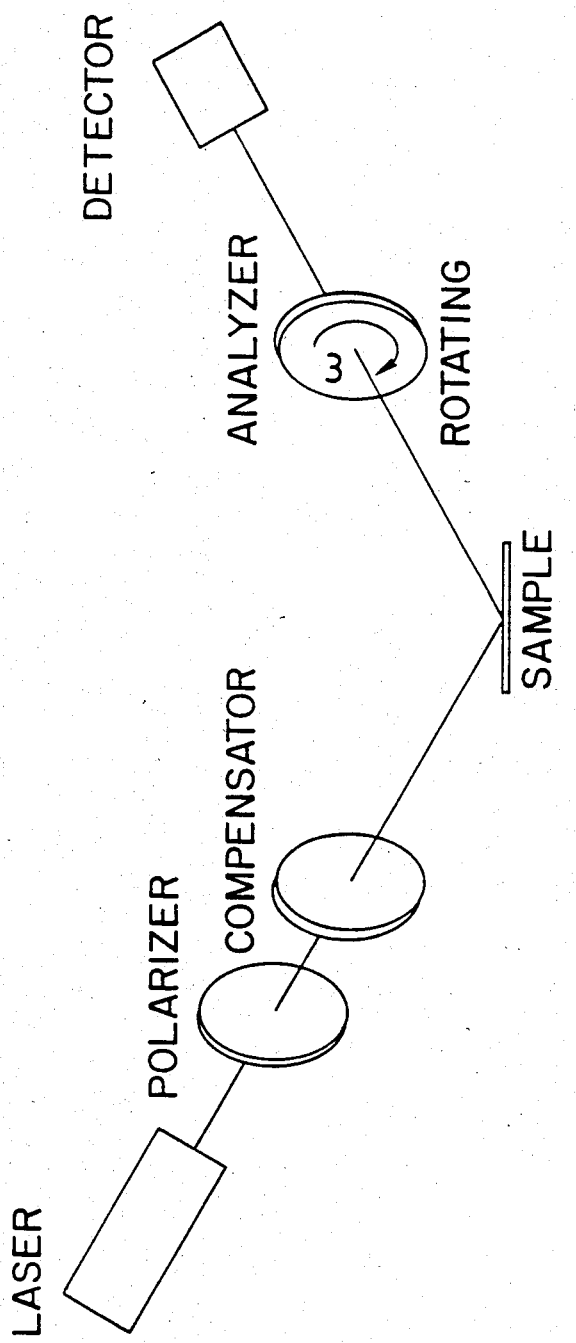
FIG. 6 is a diagram of a system of photometric ellipsometry.

Photometric ellipsometry (FIG. 6) is based on utilization of the variation of detected light intensity as a function of the polarization-ellipse parameters. In a typical case, shown in FIG. 6, the polarizer and compensator are fixed and the analyzer is synchronously rotated about the light beam axis at a constant angular velocity $\omega$. The detector signal will, therefore, exhibit periodic variations (at twice $\omega$) and is Fourier analyzed. The ellipsometric angles $\omega$ and $\Delta$ are then derived using the Fourier coefficients together with the known incident angle and the polarizer/compensator settings.

In both cases, null ellipsometry and conventional photometric ellipsometry described above, mechanical motion of components is required for instrument operation. This requirement limits the response time of the instrument and complicates its design. Data analysis in these instruments proceeds via a two-dimensional iterative technique which converts the ellipsometric angles $\psi$ and $\Delta$ to the desired material properties (i.e., refractive index, extinction coefficient, or film thickness). Because of the above-mentioned reasons (i.e., mechanical motion and slow iterative analysis), these types of ellipsometers have not found much used in realtime, online applications in a manufacturing environment.

B. Ultrafast Polarimeter

Figure 7:
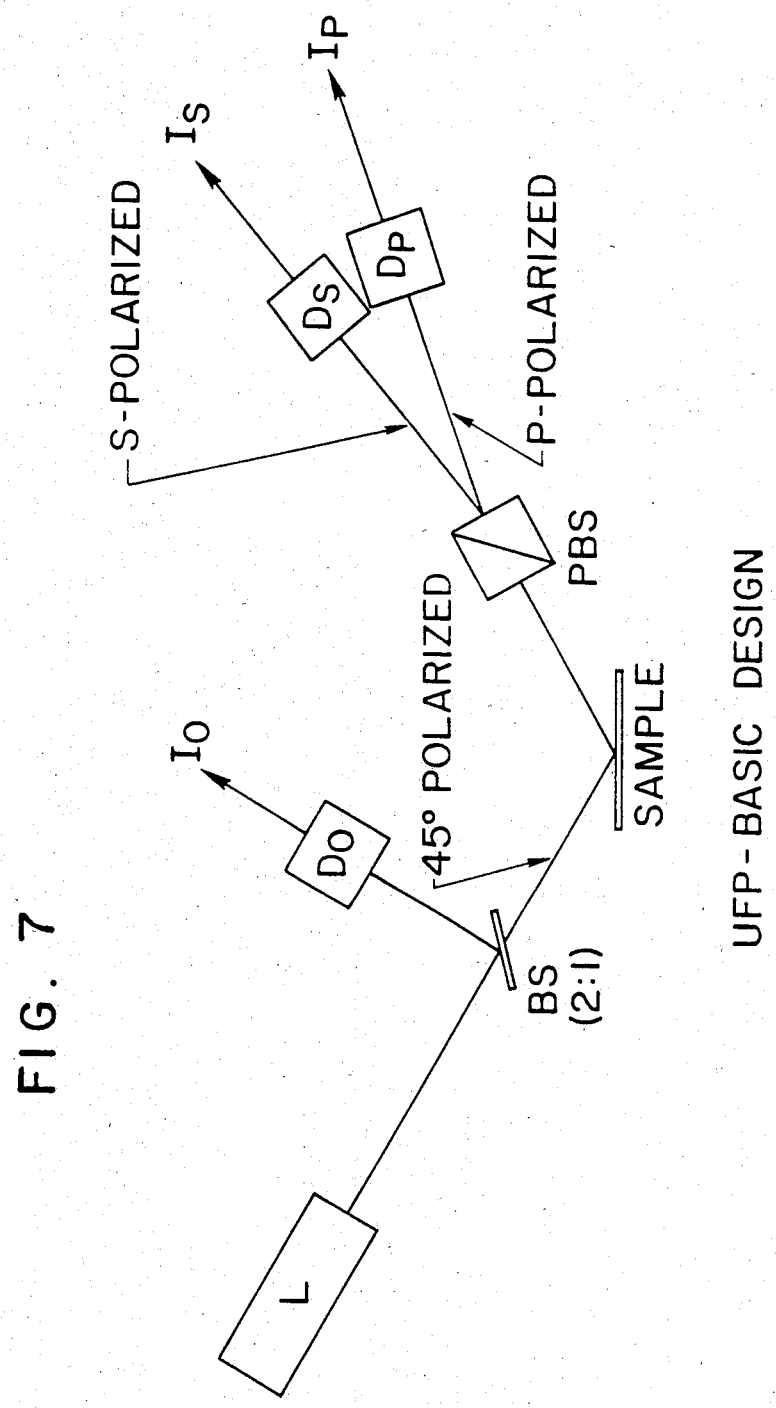
FIG. 7 is a diagram of a static photometric polarimeter in accordance with this invention.

In contrast to conventional ellipsometers, the instrument presented herein can be classified as a static photometric polarimeter. As shown in FIG. 7, the basic instrument has no moving parts and consists of a minimum number of optical components. Instrument operation proceeds, via static measurement of reflected intensities, whose polarization lie, respectively, parallel and perpendicular to the plane of incidence (the plane defined by the incident and reflected beams). Consequently, the response time of the instrument's optical section is limited only by the rise time of its photodectors. Further reduction in instrument total time response has been achieved through development of a one-dimensional data reduction algorithm as well as an algebraic solution which does not require iteration. In both cases, the measured reflected intensities are directly converted to the desired sample properties without intermediate determination of the ellipsometric angles $\psi$ and $\Delta$.

III. THE ULTRAFAST POLARIMETERS (UFP)

(Description and Analysis)

A. General

Figure 8:
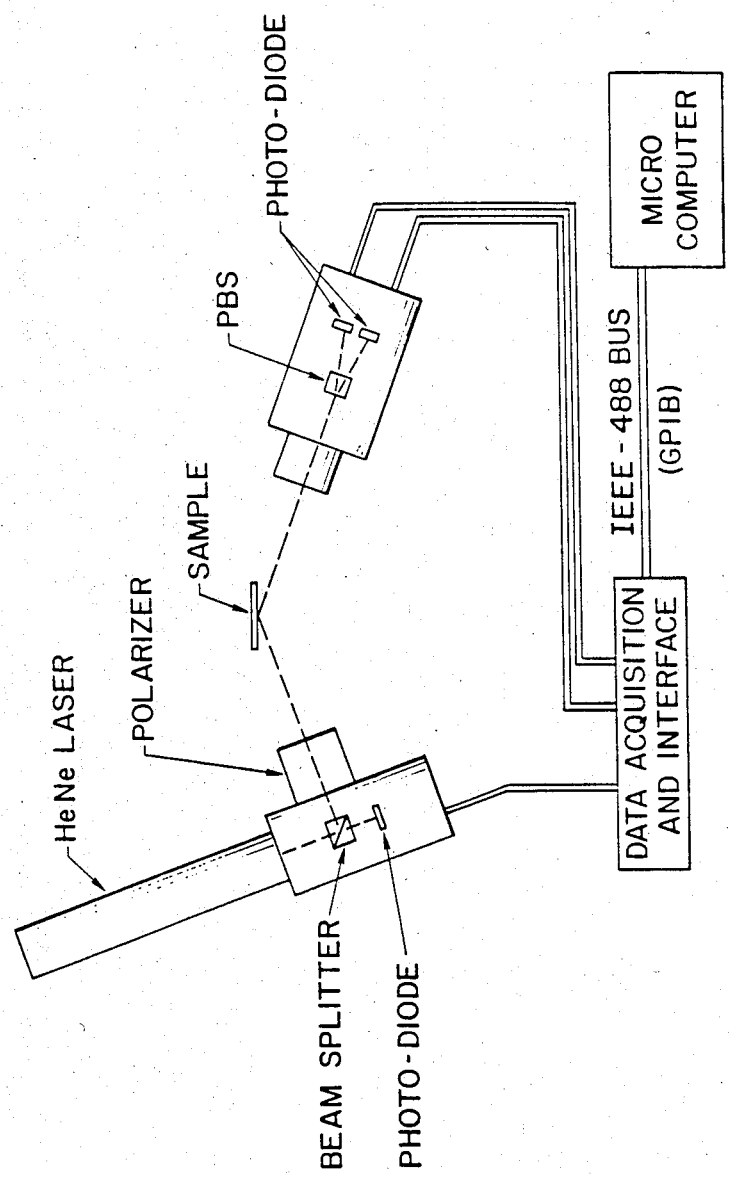
FIG. 8 is a block diagram of a polarimeter package in accordance with this invention.

The total package, shown in FIG. 8 consists of four sections:

The Optical Section—Performs the intensity measurement and provides analog output in three parallel channels.

Data Acquisition Section—Digitizes, simultaneously, the three analog signals and stores them in its own memory bank. It also provides an instrument controller interface bus.

Data Reduction Section—A software package which includes data fetching, data analysis, and display of results.

MicroComputer Section

A Hewlett-Packard HP-9836 microcomputer is currently being used to implement the software.

B. Optical Section

The optical section is a static photometric polarimeter which constantly monitors the incident beam intensity ($I_o$) and the sample-reflected intensity components ($I_p$ and $I_s$ polarized, respectively, parallel and perpendicular to the plane of incidence. From light intensities $I_o$, $I_p$, and $I_s$, recorded by detectors $D_o$, $D_p$, and $D_s$ (FIG. 7), the "p" and "s," intensity reflection coefficients (reflectances) $R_p$ and $R_s$ can be derived. For example, for an incident beam polarized at 45° to the plane of incidence and an incident beam splitting ratio of 1:2 (i.e., $I_o$ equals one-third of source intensity while two-thirds actually reach the sample), the resulting reflectances are given directly by:

$$R_p = \frac{I_p}{I_o} ; R_s = \frac{I_s}{I_o}$$

It can be shown for a sample consisting of a single interface, knowledge of $R_p$ and $R_s$ is sufficient to determine the polarization state of the reflected light. Therefore, the ellipsometric angles $\psi$ and $\Delta$ or, equivalently, the refractive index n and extinction coefficient k of the sample are functions of the reflectances (and incident angle) alone. The results are:

$$\psi = \arctan\left[\frac{R_p}{R_s}\right]^{\frac{1}{2}}$$

$$\Delta = \arccos\left[\frac{R_s - \frac{R_p}{R_s} - (1-R_p)\cos^2 2\phi}{2(1-R_s)\cos 2\phi}\left(\frac{R_s}{R_p}\right)^{\frac{1}{2}}\right]$$

where $\phi$ is the angle of incidence. The optical indices of single interface samples can be obtained directly from Fresnel Equations in terms of the reflectances by solving quadratic equations derived as follows:

$$n^2 - k^2 = 1 - 4R_s^{\frac{1}{2}} \frac{zR_s^{\frac{1}{2}} + (1+R_s)\cos\delta_s}{(1+R_s+2R_s^{\frac{1}{2}}\cos\delta_s)^2}\cos^2\phi$$

$$nk = 2R_s^{\frac{1}{2}} \frac{(1-R_s)\sin\delta_s}{(1+R_s+2R_s^{\frac{1}{2}}\cos\delta)} \text{ with}$$

$$\cos\delta_s = \frac{R_s^2 - R_p + R_s(1-R_p)\cos^2 2\phi}{2R_s^{\frac{1}{2}}(R_s-R_p)\cos 2\phi}$$

Here, $\delta_s$ is the s polarization phase shift on reflection and $\phi$ is the incident angle. Note that phase information can, therefore, be obtained directly from intensity measurements.

Note also that $\phi = 45°$, $\cos\delta_s$ is undetermined since at that angle, $R_p = R_s^2$. Consequently, reflectance measurements at this angle, on a single interface, are not independent and are, therefore, insufficient for determination of its optical properties. (This is not, however, the case for layered samples.) The above-mentioned relationship between $R_p$ and $R_s$ at $\phi = 45°$ applies to all reflecting single interfaces, independent of material properties. It can, in principle, be used for system calibration without the need for extenal standards.

The case of a sample consisting of deposited film on substrate material is more complicated. There are now five material system parameters; substrate and film optical indices ($n_s$, $k_s$, $n_f$, $k_f$) as well as film thickness ($t_f$). At a single incident angle $\phi$, the UFP performs two independent measurements (i.e., $R_p$ and $R_s$) so that only two of the five system parameters can be determined and the other threee parameters must be known (conventional ellipsometers have identical requirements). In many practical situations, the substrate's optical indices are known and the deposited film is non-absorbing (i.e., $n_s$ and $k_s$ are known and $K_f = 0$). In this most common case, the remaining film parameters ($n_f$ and $t_f$) can be determined.

C. Data Acquisition

The data acquisition section, provides several functions essential for proper instrument operations. Its main purpose is to digitize the three analog signals (intensities) provided by the optical section and transmit that raw data to the instrument controller. This section provides the following hardware features:

A/D conversion at 12 bit accuracy (i.e., 0.025%).

High-speed acquisition ($\approx 2$ microseconds/conversion).

Simultaneous acquisition in three parallel channels.

Single or multiple acquisitions (up to 256 points per channel).

Internal data storage (logic plus $3\times 2\times 256$ bytes of memory).

IEEE-488 interface bus.

In addition, optional laser shutter control (for ambient light calibration), as well as incident angle control, are available in appropriate cases.

The first three features are essential for realtime accurate data acquisition and result in total acquisition time of less than 600 microseconds (for $3\times 256$ data points at 12-bit accuracy). The fourth feature is normally used in the 'multiple' mode so that statistical analysis can be performed on incoming data. It is also used to improve the accuracy of a single measurement. The last two features were incorporated into the instrument in order to divorce the UFP from any particular controller. Data stored in its internal memory can be shipped to any controller via the IEEE-488 (also known as GPIB) interface bus.

The two optional features are available for specific applications. In most cases where ambient illumination may interfere with proper instrument operation, the ambient light can be subtracted from the measured intensities by blocking the laser input beam (via a solenoid-driven shutter), then fetching ambient data and subtracting it from the measured total intensity measurements. The incident angle control feature is available for offline applications where the optimum angle of incidence varies for different samples. It is also used in a general purpose version of UFP where multiple incident angle measurements will be used for determination of film as well as substrtate parameters without a prior knowledge of either material.

Data Reduction

Conversion of the measured quantities ($R_p$ and $R_s$ for the UFP or $\psi$ and $\Delta$ for conventional ellipsometers) to the desired material parameters, requires an appropriate algorithm. For a single interface (such as a bare substrate), an algebraic solution exists as described above. In the more general case of a substrate/film structure, a closed-form solution is generally not available and data reduction proceeds, normally, via a two-dimensional iterative algorithm. This method is adequate but not particularly suitable for realtime, online instrumentation.

For the UFP, two novel data reduction algorithms have been developed. Both convert the measured reflectances $R_p$ and $R_s$ from a transparent film on any substrate directly to the film thickness and its index of refraction. Both algorithms offer substantial improvement indata reduction time over conventional techniques. In the first method, the two-dimensional ($n_f$ and $t_f$) problem is first reduced to a one-dimensional problem (for $n_f$ only) which is then solved using a one-dimensional dynamic look-up table. The second algorithm employs a newly developed algebric solution to the reduced one-dimensional problem for film refractive index $n_f$. In both cases the film thickness $t_f$ is then derived by simple algebraic manipulations. These two data reduction algorithms have each of their own advantages and drawbacks in practice. Both are superior to conventional iterative techniques in execution times and space.

E UFP Operation

In a typical online application, the instrument is mounted externally to the chamber where film deposition (or etching) takes place. The UFP is then aligned so that the sample-reflected beam is collected by the receiving module and the angle of incidence is determined. This should be done once for each setup and checked periodically. The initial configuration parameters are then fed to the controlling computer. These include the angle of incidence and initial sample parameters; i.e., substrate optical indices as well as its film parameters (if a film exists in the initial configuration). Other required inputs for automatic operations are the sampling time intervals and the desired final film thickness. The UFP can then perform the following steps:

Start film deposition (or etching) via an appropriate signal.

Collect ambient light data using the laser shutter control.

Calibrate the system on the known initial sample configuration.

Fetch raw data at the prescribed time intervals, including rejection of inconsistent data sets and data refetching.

Correct raw data for ambient light as well as system losses.

Analyze the corrected data and derive the film's thickness and its index. Display results.

Stop film deposition (or etching) at the prescribed final film thickness.

The total turnaround time for one complete cycle (i.e., from raw data acquisition to derivation of current film thickness and refractive index) is of the order of 1 second using a microcomputer without a specialized floating point arithmetic processor.

A typical user input in a semi-automatic operation is shown in TABLE I for film deposition on a silicon substrate. The displayed results are depicted in TABLE II.

TABLE I

UFP - MANUAL OPERATION

IS THIS A CALIBRATION RUN (Y/N) ?
This is a CALIBRATION RUN. Make sure the calibration sample is mounted and the system is ready.
 computing theoretical Rp and Rs
Enter sample Phi, ns, ks, nf, tf: real

| Phi | ns | ks | nf | tf | Rpp | Rss |
|---|---|---|---|---|---|---|
| 60.00 | 3.850 | 0.020 | 1.460 | 220.0 | 0.112 | 0.569 | fetching experimental Rp and Rs

| Rp | SigRp | Rs | SigRs |
|---|---|---|---|
| 0.372 | 0.001 | 2.082 | 0.002 |

End of Calibration Run. RpCal = 3.01017E−01
 RsCal = 2.73151E−01
Read for a Data Run (Y/N) ? 'Y' mean START
 Step one: Fetching Raw Data

| Rp | SigRp | Rs | SigRs |
|---|---|---|---|
| 0.372 | 0.001 | 2.082 | 0.001 |

Step two: Computing Film Parameters
ENTER SUBSTRATE PARAMETERS Phi, nx, ks: real
 FILM THICKNESS IS 220.2 ANGSTROMS
 FILM REFRACTIVE INDEX IS 1.460
  Convergence criterion = 0.00013
  Film thickness period is = 2691.8

| Phi | ns | ks | Rp | Rs |
|---|---|---|---|---|
| 60.00 | 3.850 | 0.020 | 0.112 | 0.569 |

End of DATA RUN.

TABLE II

UFP - AUTOMATED OPERATION
This is a CALIBRATION RUN. Make sure the calibration sample is mounted and the system is ready.
Enter angle of incidence in degrees
 computing theoretical Rp and Rs
ENTER SAMPLE FILM PARAMETERS nf, tf: real

| Phi | ns | ks | nf | tf | Rpp | Rss |
|---|---|---|---|---|---|---|
| 85.00 | 3.850 | 0.020 | 1.650 | 200.0 | 0.302 | 0.0905 | fetching experimental Rp and Rs

| Rp | SigRp | Rs | SigRs |
|---|---|---|---|
| 0.77596 | 0.00121 | 0.80098 | 0.00159 |

End of Calibration Run. RpCal = 3.88934046E−01
 RsCal = 1.13016820E+00
ENTER REPETITION TIME IN SECONDS (INTEGERS, MIN OF 30)
TIME = 10:46:28
This is a DATA RUN. Make sure the data sample is mounted and the system is ready.
Previously computed calibration factors will be used
 Step one: Fetching Raw Data

| Rp | SigRp | Rs | SigRs |
|---|---|---|---|
| 0.79385 | 0.00141 | 0.79298 | 0.00183 |

Step two: computing Film Parameters
 FILM THICKNESS IS 219.5 ANGSTROMS
 FILM REFRACTIVE INDEX IS 1.610
  Convergence criterion = 0.35337
  Film thickness period is = 2501.6

| Phi | ns | ks | Rp | Rs |
|---|---|---|---|---|
| 85.00 | 3.850 | 0.020 | 0.309 | 0.896 |

End of DATA RUN.

F The Software Package

All software routines were written in PASCAL for the following reasons:

PASCAL is a compiled language, resulting in fast execution.

Pascal is a structured language, resulting in ease of program comprehension, modification, or translation to other languages.

PASCAL is readily available on all modern microcomputers including IBM's Personal Computer and Series/1 mini-computer.

The total software package consists of a control program (UFP.RUN 02) and five modules which contain the various procedures and functions necessary for proper instrument operation. It is currently implemented on the IBM Series 1 microcomputer. It was previously implemented on the Hewlett Packard AP9836 microcomputer, IBM PC and IBM Series 1 based development system, and the IBM PC and can be easily converted to other controllers. The required modules are:

UFP.CALIB: Instrument Calibration
CALCFILM
UFP.FETCH02:
 (i) Data acquisition (raw data or ambient data)
 (ii) Statistical data evaluation.
UFP.ANAL2: Data analysis (dynamic look-up table or algebraic solution).
UFP.ST02
MATH.LIB: Statistical and complex math routines.

G Error Analysis

Three sources of errors affect proper operation of any instrument. These are transient errors, random errors, and systematic errors. The first is difficult to detect (or control other than by careful design), the second affects instrument precision (via statistical fluctuation in measured parameters), and the third affects instrument accuracy (i.e., determination of the true value of measured parameters).

Transient errors occur due to nonstatistical "random" fluctuations in measured parameters (line voltage fluctuation, RF and LF interference, etc). In addition to careful circuit design, transient effects have been minimized via multiple measurements of each data point. In normal operation, each data fetch consists of 256 measurements. The standard deviation of this 256-point sample is calculated as well as its mean. Data sets which exhibit a standard deviation of more than 0.25% (or other user-defined limit) are rejected and immediately refetched. Thus, to some degree, transient error effects are minimized. Since data fetching takes less than 600 microseconds (at 2 micro-second per measurement), the effect on instrument operation is negligible in practical cases.

Random errors are statistical in nature and can also be minimized via multiple measurements. In normal operation, the statistical average (sample mean) is used in data analysis. Thus, the error due to a single measurement is reduced by a factor of 16, which is the square root of the number of measurements (i.e., sample size). Since random errors affect instrument precision (or repeatability), a series of measurements was taken over several hours at 5-minute intervals. The results indicate repeatability of better than 5 Å, well within Manufacturing tolerances.

Systematic errors are, by far, the largest source of instrument error. They can be caused by instrument misalignment as well as system losses and distortions. This is particularly important in the case of a photometric instrument, such as the UFP, which is normally mounted externally to the chamber and experiences unavoidable optical losses in entrance and exit ports. Ambient light also affects intensity measurements and must be eliminated or taken into account.

Instrument alignment is straightfoward. The incident beam must be polarized at 45° to the plane of incidence (circularly polarized beam can also be used with identical results). This is done once, at initial setup (or before instrument assembly). The receiving unit is also aligned to properly intercept and detect the reflected beam. Perfect alignment of the instrument is not necessary since small misalignments are automatically corrected at the calibration step (provided they do not change with time). Instrument calibration is the most important step in minimization of systematic errors. In fact, instrument performance depends mostly on its calibration. For this reason, the calibration step is the last step before start of film deposition (or etching) and is performed on the initial sample configuration. Based on the known optical properties of the initial samples and intensity data fetched by the instrument, correction factors are calculated. These factors correct for all constant optical losses in the system including small instrument misalignment and chamber port losses (as well as small light-scattering losses). It is also possible to calibrate the instrument during the first seconds of deposition (or etching) so that whatever changes might be taking place on turning on the film deposition or etching process will be corrected at the calibration step.

Ambient light is normally eliminated by proper enclosed design of the photodetector assembly. In addition, a narrow-band ("notch") optical filter, centered at the HeNe light wavelength (632.8 nm), is incorporated into the receiver section, thus eliminating the ambient. In those cases where non-negligible ambient intensities exist at the HeNe wavelength and cannot be filtered out, the optional laser shutter is used to fetch ambient light intensities which are subtracted from all measured intensities prior to data manipulation.

Total instrument performance was derived empirically using calibration standards as well as in situ runs on a sputtering chamber and an oxidation furnace. In all cases, overall accuracy was better than 5% (typically 3%) for films over 100 Å in thickness.

IV EXPERIMENTAL RESULTS AND EVALUAIION

A. General

The UFP is a complete instrument designed specifically for online measurements. The various instrument sections have been tested separately. However, the only reliable way of evaluating its total performance is by measuring a number of samples under a variety of conditions and comparing the results with measurements by other instruments. This was done both offline on several "standards" and online in a sputtering chamber and a silicon oxidation furnace. In all cases, agreement between MRL's UFP measurements and independent measurements by internal and commercial ellipsometers was good.

B Offline Testing

Testing of total instrument performance consisted of two tests—a Precision Test and an Accuracy Test.

Figure 9:
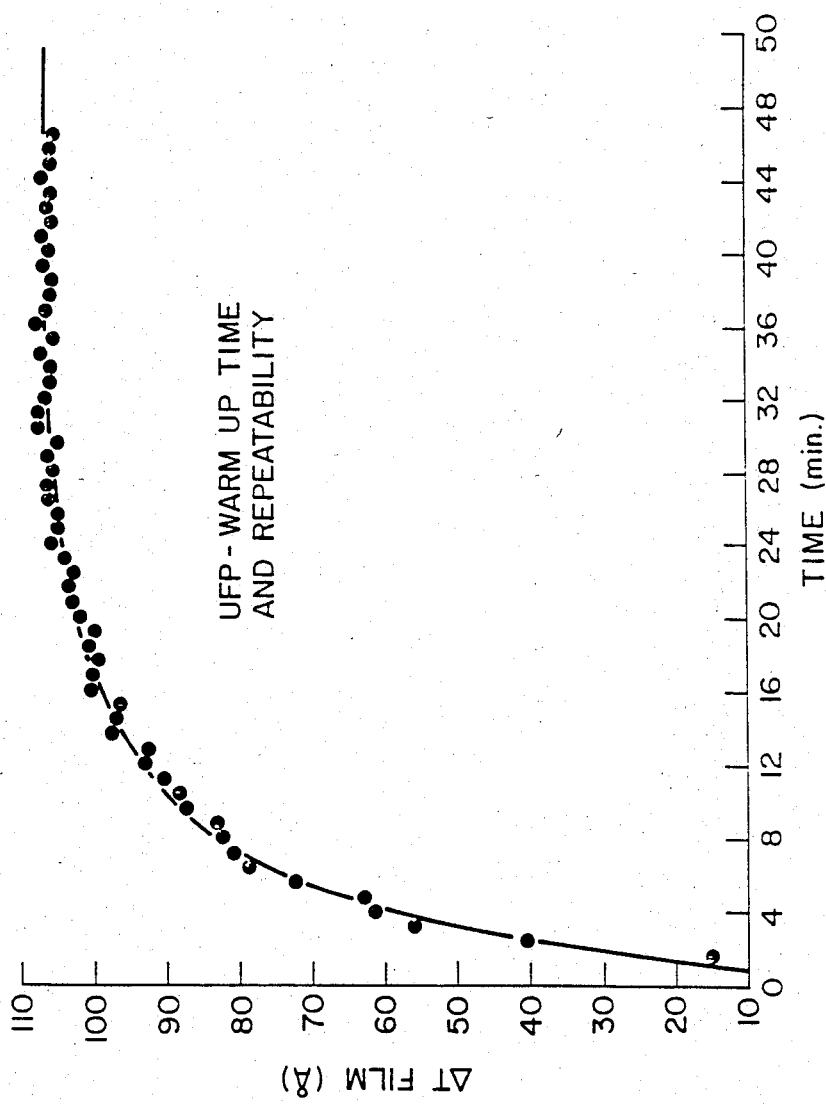
FIG. 9 is a curve of thickness variation from the initial measurement as a function of time.

Instrument precision (i.e., repeatability), as well as its warm-up time, is shown in FIG. 9. An arbitrary sample was mounted and the instrument was turned on from a "cold" start. Data was collected and analyzed, automatically, at rescribed intervals of 30 seconds. The results were plotted as thickness variation (from the initial state) versus elapsed time. Clearly, instrument warm-up time is about 20 minutes while its precision is better than 5 Å. This test was repeated on a variety of samples and time intervals with the same conclusions.

Instrument accuracy was tested using seven samples plus an accurately measured calibration "standard." All samples consisted of thermally oxidized silicon wafers with $SiO_2$ film thickness ranging from 220 Å to about 6900 Å. These samples were measured by the UFP as well as by four other instruments which included a commercial (Rudolph Res Model RR200) ellipsometer, two separate ETA ellipsometers and a film thickness analyzer (FTA). The results are shown in TABLE III together with the UFP results. The agreement is clearly good over the entire thickness range. In all cases, the chosen angle of incidence was 70° (except for the FTA which requires normal incidence and knowledge of the film refractive index). Similar results were obtained by the UFP operating at other angles of incidence.

TABLE III

| UFP RESULTS COMPARISON | | | | | |
|---|---|---|---|---|---|
| WAFER NO. | $\epsilon TA1$ Å | RUDOLPH Å | $\epsilon TA2$ Å | FTA Å | UFP Å |
| 1 | 230 | 223.2 | 245 | 219 ± 4 | 223.4 |
| 2 | 388 | 370.1 | 393 | 387 ± 3 | 375.5 |
| 3 | 499 | 458.7 | 481 | 473 ± 1 | 478.0 |
| 4 | 932 | 878.4 | 930 | 929 ± 1 | 935.4 |
| 5 | 2137 | 2228.0 | 2144 | 2135 | 2150.0 |
| 6 | 3162 | 3147.0 | n/c | 3159 | 3176.0 |
| 7 | 6921 | 6479.0 | n/c | 6883 | 6915.0 |

C Online Testing (Sputtering Chamber)

Figure 10:
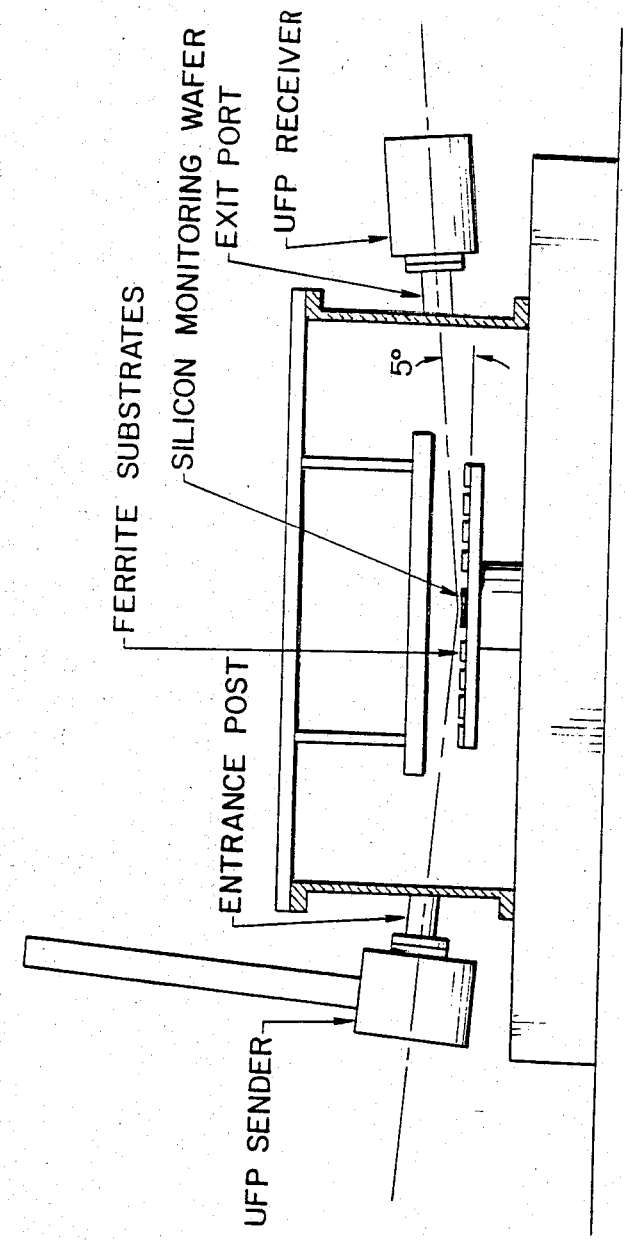
FIG. 10 is an on-line testing system in accordance with this invention showing the source of light and the UFP Receiver on opposite sides of the sputtering chamber.
Figure 11:
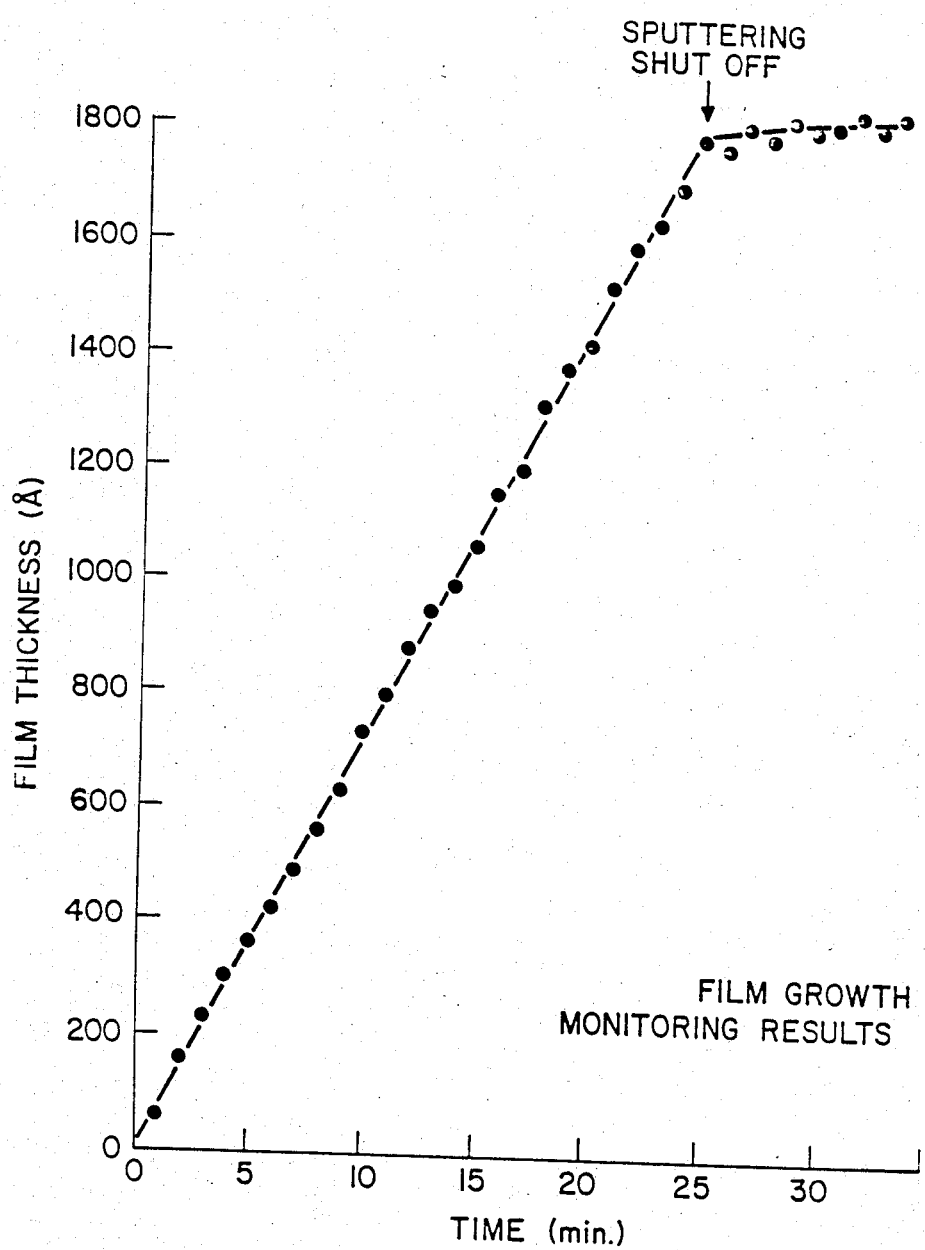
FIG. 11 shows film thickness as a function of time for the system of FIG. 10.

This test was performed on a Perkin-Elmer sputtering chamber used in a manufacturing line to deposit $Al_2O_3$ film on ferrite substrates. The chamber has existing entrance and exit ports (with Pyrex[R] windows) which restrict the incident angle to 85° (i.e., 5° grazing angle) as shown in FIG. 10. The instrument was mounted externally to the chamber and was aligned to a silicon monitoring wafer at the center of the sample table. The instrument was calibrated on the "bare" wafer immediately after the start of $Al_2O_3$ sputtering. Data were fetched and analyzed at 1 minute intervals thereafter. Growth of the film is depicted in FIG. 11. At the end of the "run," the sputtering unit was turned off but the UFP continued monitoring for a few minutes until film thickness measurement remained constant. The sample was then taken out and measured on a commercial (Gaertner) ellipsometer and compared with the final UFP results. Agreement between the two instruments was very good (about 3%) considering the extremely shallow incident angle used by the UFP. This test was repeated several times for different sputtering runs with similar results. See Table IV.

TABLE IV
REAL TIME FILM GROWTH MONITORING IN TUCSON

TIME = 10:55:28
This is a DATA RUN.
Previously computed calibration factors will be used Step one: Fetching Raw Data

| Rp | SigRp | Rs | SigRs |
|---|---|---|---|
| 1.31377 | 0.00228 | 0.68345 | 0.00164 |

Step two: Computing Film Parameters
FILM THICKNESS IS 532.3 ANGSTROMS
FILM REFRACTIVE INDEX IS 1.610
Convergence criterion = 1.34392
Film thickness period is = 2501.6

| Phi | ns | ks | Rp | Rs |
|---|---|---|---|---|
| 85.00 | 3.850 | 0.020 | 0.511 | 0.772 |

End of DATA RUN.
TIME = 10:56:28
This is a DATA RUN.
Previously computed calibration factors will be used Step one: Fetching Raw Data

| Rp | SigRp | Rs | SigRs |
|---|---|---|---|
| 1.35226 | 0.00236 | 0.66335 | 0.00161 |

Step two: Computing Film Parameters
FILM THICKNESS IS 559.4 ANGSTROMS
FILM REFRACTIVE INDEX IS 1.610

D Online Testing (Oxidation Furnace)

This test was performed in a silicon facility on an oxidation furnace operating at 1000° C. Since access to the tubular furnace was restricted to a single port, normal single reflection monitoring could not be used. Instead, two monitoring wafers were used in a retroreflective mode so that the incident beam underwent two reflections and returned (parallel to the incident beam) via a single access port. The monitoring wafers were positioned perpendicular to each other and aligned with respect to the incident beam, resulting in a 45° beam incident angle for both. The software package was modified to account for the double reflection. The effects of the considerable amount of ambient light (due to thermal radiation from the furnace) were compensated in two ways. An optical "notch" filter, centered at the HeNe wavelength, reduced the ambient to a low level which was then eliminated on each photodetector by appropriate control of the photodiodes' bias circuitry (laser shutter control was not available at the time). The quartz boat containing the two-wafer setup was inserted into the hot zone of the furnace with nitrogen gas as oxidation inhibitor. After alignment and ambient subtraction, the UFP performed its calibration on the "bare" substrate. Oxygen was then introduced into the furnace and oxide thickness was monitored at 1-minute in tervals. At the end of the run, the samples were removed and measured on an available ETA ellipsometer. The ETA and UFP were in good agreement. This test was performed during both "dry" and "wet" oxidation runs with good end results.

F Performance Evaluation

The UFP has been tested under a variety of conditions both offline and online. During testing, several observations were made which relate to instrument performance and should be kept in mind by users.

Calibration—Instrument accuracy is a direct function of its calibration. Best results are obtained using calibration on "bare" samples or an accurately known filmed substrate (any calibration "standard" can be used. It need not be of the same composition as the monitored sample). "Thin" calibration standards are preferred.

Thin Films—The accuracy of the UFP is better than 5% for films whose thickness is larger than 100 Å. For thin films (below 100 Å), the fractional (percent) accuracy gets progressively worse as film thickness approaches zero. In these cases, knowledge of the film's refractive index may be required for accurate determination of film thickness.

Online Monitoring—Best results are obtained when the calibration step is performed immediately after start of film deposition process. This ensures proper calibration under true deposition conditions.

Light Scattering—Best results are obtained on samples which do not scatter light appreciably. Light scattering effects are not, normally, a problem in online monitoring where the instrument is calibrated on the very substrate on which deposition takes place. Offline measurement may result in reduced accuracy if calibration and measurement are performed on materials with different scattering characteristics.

Film "Periodicity"—As in all ellipsometric measurement techniques, the measured parameters exhibit periodicity so that offline thickness measurements result in the usual ellipsometric ambiguity. For online measurements, this is not a problem, however, because the instrument controller can keep track of the number of film thickness periods accumulated and display only the true film thickness.

V Applications

A General

The UFP has been designed for online film thickness monitoring in manufacturing where its current applications are. These applications, at this time, consist of monitoring film growth in a chamber or furnace. The instrument, however, is capable of other applications which utilize its fast response time and its design flexibility to monitor changes in film or substrate composition changes which affect their optical properties. A nonexhaustive list follows.

B Online Film Growth

This application has been demonstrated (Section IV) in two environments—a sputtering chamber ($Al_2O_3$ deposition) and oxidation furnace (thermal $SiO_2$ growth). In both cases, direct film thickness monitoring was achieved independent of deposition rate.

C Online Film Etching

Operationally, this application is identical to the previous one since UFP monitors film thickness directly. Removal of a prescribed film thickness requires only that the initial sample configuration be known.

D End-Point Detection

Accurate end-point detection is feasible either as a special case of online etch monitor or simply by direct monitoring of the reflectances $R_p$ and $R_s$. This is a more sensitive technique than simple reflectance monitoring which measures the average $R_p$ and $R_s$.

E Surface Changes

Tracking of fast changes in surface conditions, due to physical or chemical interactions, can be monitored with a 2-microsecond resolving time. The need for microsecond tracking of changes in a metallic film undergoing fast melting (1 millisecond laser melting pulse) did, in fact, prompt the investigation which led to the development of the UFP. Surface or film composition changes can be monitored as they occur.

F Offline Measurements

A general purpose version of the instrument is available. This is a stand-alone unit capable of normal offline ellipsometric measurements of surfaces and films. In addition, this unit has programmable angle-of-incidence capabilities so that optimum incident angle can be programmed in specific cases for best results.

Figure 12:
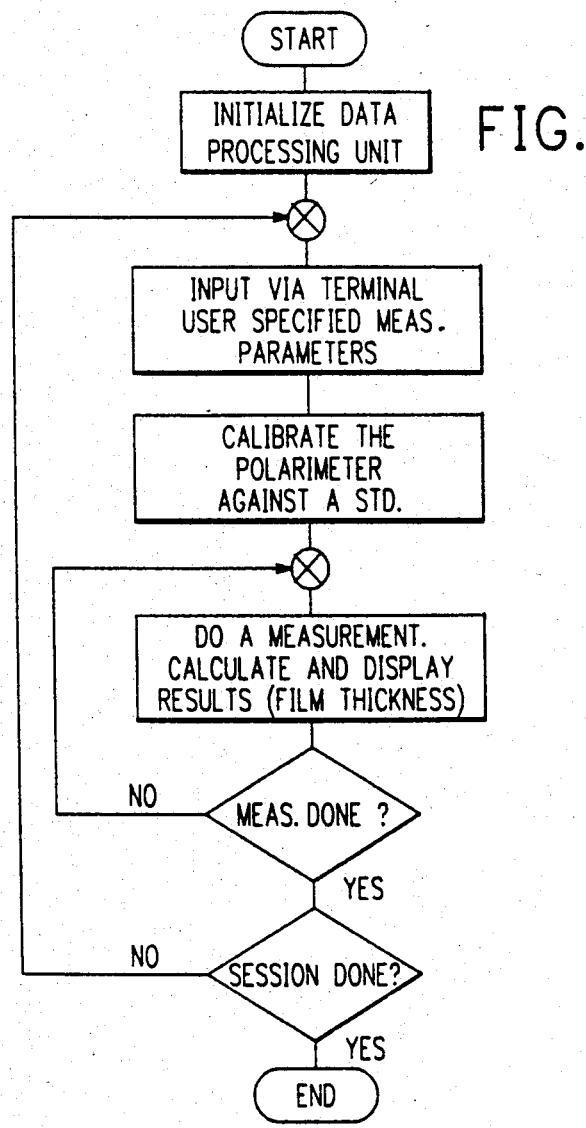
FIG. 12 shows a block diagram of the program structure for operations which can be performed by the system.

FIG. 12 shows the polarimeter control sequence for the software system which utilizes the programs which are included in the applications program 42.

Figure 13:
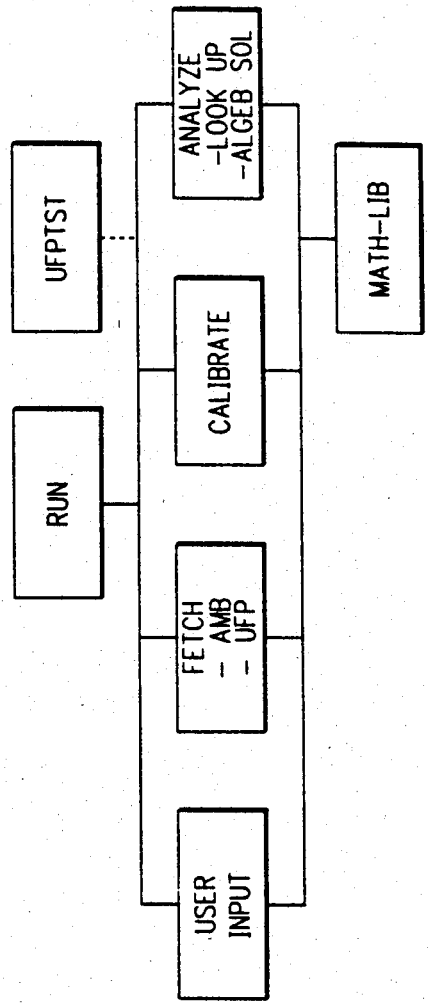
FIG. 13 shows the program structure with linkages for two different operations which can be performed by the system.

FIG. 13 shows the program structure for two different operations which can be performed by the system with the linkages between the programs used. For example, the run program invokes the sequential operation of the programs on the User Input to Analyze Line. The Fetch to Analyze programs all invoke the math-lib program through the linkages shown when they require the functions provided by the Math-Lib program. The application program included in the system is comprized of several modules or segments which are integrated into one applications program. The segments identified as UFPANAL02 S1PASCAL and CALCFILM S1PASCAL performs the calculations which are used in the equations which make the measurements possible with the system of this invention. The program uses RP which stands for "$r_p$", RS which stands for "$r_s$", NF which stands for "$n_f$", TF1 which stands for a film thickness parameter, TF2 which stands for a film thickness parameter, and TFREF which stands for a film thickness parameter.

The segment UFPRUN02 is the main-line program used to control the operation of the polarimeter. Looking at the code which is listed in the appendix for the program in question, the first command is USERINPT which is used to enter data such as the variables of the system. This can be eliminated in the automatic system.

Next is GPIBINIT which initializes the General Purpose Interface Bus 35 in FIG. 4.

The third command is CLS (Clear Screen).

Fourth is RDCHAR (Read character-inputs (by-passed in automatic mode)

UPFETCH (Fetch Measurement Data from the polarimeter).

AMBFETCH (Fetch Ambient Data from the polarimeter).

SETRATE (Set measuring rate for taking a measurement 256 times at a single point on the surface). Preferably, the measurements are repeated 256 times at 2 microsecond or 100 millisecond intervals.

UFPCALIB (Calibrate on bare substrate first before deposition commences.)

Numerous other functions follow in order, and the program will perform the calculations desired.

The ROM 34 in the control logic Z80 carries the Ellipse 4 Assemble program which is included in the appendix, and which controls the operation of the data processing unit 30.

References

1. J. D. Jackson, Classical Electrodynamics, Wiley (1975) pp. 278–82.
2. P. S. Hauge, Techniques of Measurement of Polarization—Altering Properties of Linear Optical Systems, SPIE 112, Optical Polarimetry (1977).
3. P. S. Hauge, Survey of Methods for the Complete Determination of a State of Polarization, SPIE 88, Polarized Light (1976).
4. R. M. Azzam and N. M. Bashara, Ellipsometry and Polarized Light, North-Holland (1977).
5. V. Brusic, The Application of Intensity Transients in Ellipsometry, Appl. Opt. 9, No. 7 (1970).

Industrial Applicability

Technical advantages of the instant invention are as follows:
(1) requires less hardware,
(2) more accurate
  (a) independent of uniformity of beam
  (b) alignment of beam is not critical
  (c) does not assume uniformity of sample over large area,
(3) allows small beam size,
(4) allows addition of focussing lens for improved performance,
(5) allows high speed, very accurate measurements—no moving parts,
(6) provides in situ, real time measurements for experiments or process monitoring and control in film growth studies.

Having thus described our invention, what we claim as new, and desire to secure by Letters Patent is:

1. An instrument for the static measurement of reflected intensities whose polarizations lie, parallel and perpendicular to the plane of incidence comprising:
  (a) a source of a polarized beam,
  (b) a first beam splitter for splitting said polarized beam towards a detector ($D_o$) and a sample,
  (c) means for supporting said sample in the path of the beam,
  (d) a second polarizing beam splitter for direct reception of the reflection of said beam from the surface of a sample in said sample position, and two detectors to receive only the parallel ($D_p$) and perpendicular ($D_s$) polarization components of said reflected split beam for computation of the index of refraction and film thickness of said sample by knowing the light intensities $I_o$, $I_p$ and $I_s$ associated with the respective detectors and without mechanical motion of the instrument components and without intermediate determination of the ellipsometric angles, ellipse orientation ($\psi$), elliptical phase difference ($\Delta$).

2. An insturment is accordance with claim 1 wherein said source includes means for polarization of said light beam.

3. An instrument in accordance with claim 2 wherein said means for polarization polarizes said light beam at 45°.

4. An instrument in accordance with claim 2 wherein said means for polarization provides circular polarization of said light beam.

5. An instrument in accordance with claim 1 wherein the polarized light beam is directed at the sample at an angle of 5° to 90°.

6. An instrument in accordance with claim 5 wherein the polarized light beams is directed at the sample at an angle of incidence of 70°.

7. An instrument in accordance with claim 1 wherein the beam reflected from the surface of the sample is passed through an aperture located in front of the beam splitter.

* * * * *